United States Patent [19]

Suzuta et al.

[11] Patent Number: 4,483,928

[45] Date of Patent: Nov. 20, 1984

[54] MICROCAPSULES SENSITIZED WITH ANTIBODY AND A METHOD FOR MEASUREMENT OF LYMPHOCYTE USING THE SAME BASED ON CELL-MEDIATED IMMUNITY

[75] Inventors: Tatsuo Suzuta, Tokyo; Nobuo Hiratsuka, Saitama, both of Japan

[73] Assignee: Fuji Photo Film Co., Ltd., Saitama, Japan

[21] Appl. No.: 415,300

[22] Filed: Sep. 7, 1982

[30] Foreign Application Priority Data

Sep. 7, 1981 [JP] Japan .................................. 56-140668

[51] Int. Cl.³ .............................................. G01N 33/54
[52] U.S. Cl. ..................................... 436/519; 436/520; 436/829
[58] Field of Search ........................ 436/519, 829, 520

[56] References Cited

U.S. PATENT DOCUMENTS 4,267,234  5/1981  Rembaum ....................... 428/407 X
4,342,739  8/1982  Kakimi ................................ 436/823

OTHER PUBLICATIONS

Chemical Abstracts, 89:58222c (1978).

*Primary Examiner*—Sidney Marantz
*Attorney, Agent, or Firm*—Sughrue, Mion, Zinn, Macpeak, and Seas

[57] ABSTRACT

Microcapsules are sensitized with antibody to antigen of lymphocyte. Using such microcapsules, B cells and/or T cells can be selectively measured separately or simultaneously, in a simple manner, based on cell-mediated immunity which comprises applying the microcapsules sensitized with antibody to antigen of lymphocyte and sheep red cells or another kind of antibody-sensitized microcapsules that are optically distinguishable from the first antibody-sensitized microcapsules, to lymphocyte at the same time and thereafter independently measuring respective cells that are optically distinguishable from each other.

The operation for the measurement is extremely simple and neither skill nor special equipment is required.

8 Claims, No Drawings

MICROCAPSULES SENSITIZED WITH ANTIBODY AND A METHOD FOR MEASUREMENT OF LYMPHOCYTE USING THE SAME BASED ON CELL-MEDIATED IMMUNITY

BACKGROUND OF THE INVENTION

1. Field of the Invention

The present invention relates to microcapsules sensitized with antibody and an improved method for cell-mediated immunity measurement of lymphocyte using such microcapsules. More particularly, the present invention relates to microcapsules sensitized with antibody to antigen of lymphocyte, and, a method for measuring lymphocyte using the foregoing microcapsules based on cell-mediated immunity and sheep red cells, a method for measuring lymphocyte using at least two kinds of the foregoing microcapsules, based on cell-mediated immunity, which are distinguishable from each other, and further a method for the measurement of B cells of lymphocyte using microcapsules sensitized with antibody to antigen of B cells of lymphocyte.

2. Background of the Invention

The term "cell-mediated immunity" is well established in the art and refers to specific immunity which is mediated by small lymphocytes (cells of 6 to 8 μm in diameter with a deeply-stained nucleus and narrow rim of cytoplasm), and is dependent on the presence of the thymus at birth. Cell-mediated immunity is responsible for reactions such as delayed hypersensitivty, tuberculin test reactions, immunodeficiency, etc. and is important in defense against viral infections and against some bacteria.

To immunologically identify or measure T cells (thymus derived cells, also called lymphoid cells that have been demonstrated to be derived from the thymus) and B cells (bone marrow derived cells; lymphocytes found in the peripheral lymphoid organs, i.e., spleen and lymph nodes, etc. which are known to be derived from the bone marrow, but has not been processed by the thymus) of human lymphocytes in the clinical field, the identification or measurement of T lymphocytes (T cells) has been hitherto performed generally by the E rosette technique; B lymphocytes (B cells) have been identified or measured by detecting Fc receptor (receptor for Fc fragment or crystallizable fragment obtained by papain hydrolysis of immunoglobulin molecules) or C3 receptor (receptor for the third component of complement) according to the EA (short for ovalbumin obtained from the avian egg) or EAC (short for erythrocyte antibody complement) rosette technique or by detecting immunoglobulins at the surface of cell membrane according to the fluorescent antibody technique. These methods are based on most fundamental reactions in cell-mediated immunity; in recent years, these methods have been widely utilized in routine tests as determining a proportion of T cells to B cells that are inevitable for the presumptive observation of the immune function of the patient. However, as long as the prior art methods are utilized, T and B cells must be identified or determined separately using independent plates. In addition, the identification of B cells requires complicated procedures. That is, sheep red cells bind to T cells as they are; accordingly, they should be inactivated to T cells and then chemically changed so as to have a binding site for B cells. These procedures also involve poor detection sensitivity. Furthermore, when the fluorescent antibody technique is utilized, relatively large amounts of a testing sample are required so that physical load of the patient becomes serious, and, not only special equipments or facilities are necessary but also technical skill is required for operations of these methods. Such restrictions are problems encountered in these methods.

Further in the E rosette technique and the EA rosette technique or the EAC rosette technique, red cells of animals are employed and hence, these techniques involve problems that extremely complicated operations are required for the preparation of a red cell suspension and moreover, it is impossible to store red cells for long periods of time.

It has been found that T cells and B cells of lymphocytes and other cells can be identified or measured with a single operation simultaneously in a simple operation using an extremely small quantity of a testing sample as compared to the prior art methods, by performing an immune response using one kind or plural kinds of microcapsules sensitized with antibody to antigen of lymphocytes, alternatively, together with sheep red cells or by bringing such microcapsules into contact with lymphocyte adhered to a microplate, etc., and the present invention has thus been accomplished.

Microcapsules having bound thereto an antigen or antibody at the surface thereof are disclosed in U.S. Pat. No. 4,342,739. However, these microcapsules are utilized for the determination of serum components based on cell agglutination, not for the determination of lymphocytes through the rosette formation techniques.

SUMMARY OF THE INVENTION

An object of the present invention is to provide a method for the measurement of various kinds of lymphocytes in a single operation.

Another object of the present invention is to provide a method for the measurement of various kinds of lymphocytes accurately in a simple manner using a conventional optical microscope without requiring any dark room or any expensive fluorescence microscope.

A further object of the present invention is to provide a method for the measurement of a variety of lymphocytes in which a step of removing macrophage from the lymphocytes is omitted because the macrophage having phagocytosis is visually distinguishable due to an intake of the microcapsules into the macrophage.

A still further object of the present invention is to provide a method for the measurement of various kinds of lymphocytes always with high accuracy and good reproducibility by the use of microcapsules synthesized to be sensitized with antibodies to antigens of various kinds of lymphocytes since the antibodies can be stored extremely stably for long periods of time.

A still further object of the present invention is to provide microcapsules sensitized with antibody to antigen of lymphocyte which are useful for the foregoing various objects.

A still further object of the present invention is to provide microcapsules having incorporated a coloring agent in the core thereof and having sensitized with antibody to antigen of lymphocyte at the outer wall thereof.

PREFERRED EMBODIMENTS OF THE INVENTION

The present invention is characterized by:

(1) A microcapsule sensitized with antibody to antigen of lymphocyte.

(2) A method for measuring T cells and/or B cells based on cell-mediated immunity which comprises applying a microcapsule sensitized with antibody to antigen of lymphocyte and sheep red cells to lymphocyte at the same time and then independently measuring distinguishable cells from each other.

(3) A method for measuring T cells and/or B cells based on cell-mediated immunity which comprises applying to lymphocytes, at the same time, at least two kinds of microcapsules sensitized with at least two kinds of antibodies to the corresponding antigens of lymphocytes that are optically distinguishable from each other and, thereafter independently measuring the cells that are optically distinguishable; and;

(4) A method for the measurement of B cells based on cell-mediated immunity which comprises applying to lymphocyte microcapsules sensitized with antibody to antigen for B cells of the lymphocyte, and thereafter measuring B cells that are distinguishable.

The microcapsules in accordance with the present invention is effective for the measurement of T cells and/or B cells of lymphocytes in a single operation, utilizing the rosette formation technique. The rosette formation technique is also called immunocyto-adherence which is a technique by which cells which carry immunoglubulin on their surfaces (either because they have formed the immunoglobulin or because it has become bound to the cell) can be detected. Red cells coated with antigen, e.g., sheep red cells, are mixed with the cells and bind to the microcapsules bearing antibody to form a rosette. The rosettes are put on a microscope slide by cytocentrifuge, the cell at the center (i.e., T cell when sheep red cells are employed, or B cell when microcapsules sensitized with, e.g., anti-IgG antibody, are employed) is stained and identified. Details of the rosette formation technique is described in Van Oers et al., *Eur. J. Immunol.*, 7, 143 (1977), which disclosure is hereby incorporated by reference.

The term "applying" as used herein refers to a state of bringing the microcapsules of the present invention into contact with lymphocytes, most typically mixing of the microcapsules with lymphocytes.

The term "sensitized" as used herein refers to a state where antibody is bound as a preliminary step in elicitation of an immunological reactions and the term "sensitized microcapsules" refers to microcapsules to which antibody to antigen of lymphocyte is bound and have become immunologically activated (primed) by administration of antigen of lymphocyte. The sensitized microcapsules are ones that have been specifically activated in respect of a given antigen and can mediate the reactions of cell-mediated immunity.

Typical examples of antibodies which can be employed in accordance with the present invention include anti-IgG antibody, anti-IgM antibody, anti-IgA antibody, anti-T antibody and other antibodies to brain common antigen, thymus common antigen, etc. as surface antigens of lymphocytes. Of these, anti-IgG antibody, anti-IgM antibody and anti-IgA antibody possess receptors for B cells of lymphocytes so that the microcapsules sensitized with these antibodies can form rosettes with B cells. On the other hand, when microcapsules sensitized with anti-T antibody or antibodies to brain common antigen and thymus common antigen are employed, these microcapsules can selectively form rosettes with T cells since these antibodies have receptors for T cells.

Coloring agents preferably employed for coloring the microcapsules of the present invention can have any color hue. However, in the case of performing the measurement in the presence of sheep red cells, the color hue should be one that provides easier discrimination, not a color hue similar to that of sheep red cells. Further, also in case where two or more kinds of microcapsules are employed, it is also needless to say that color hues distinguishable from are another be selected.

In the present invention, coloring agents which can effect easier measurement or determination can be incorporated in the core material of the microcapsule. It was difficult to use synthesized, packed fine particles conventionally employed in the prior art—that were colored with coloring agents—for practical purpose because the coloring agents were directly brought into contact with antibody to antigen of lymphocyte so that they adversely affected the antibody in most cases. To the contrary, coloring agents can be incorporated in the core material in the microcapsules, and, the wall materials are composed of resins alone. That is, the surface of each of the microcapsules is covered with resins and, by appropriately choosing resins, it is possible not to adversely affect antibody in the present invention.

Coloring agents which can be employed in the present invention for purpose of improving contrast in distinguishing one from another are oleophilic coloring dyes and specific examples thereof include Color Index Solvent Red Nos. 1, 3, 8, 23, 24, 25, 27, 30, 49, 81, 82, 84, 100, 109 and 121; Color Index Solvent Violet Nos. 8, 13, 14, 21 and 27; Color Index Solvent Blue Nos. 2, 11, 12, 25, 35, 36, 55 and 73; Color Index Solvent Green No. 3; Color Index Solvent Brown Nos. 3, 5, 20 and 37; Color Index Solvent Black Nos. 3, 5, 7, 22, 23 and 123, C.I. Solvent Blue (C.I. #61525) etc. These coloring agents are chosen depending upon purpose and incorporated into the core material in the present invention so that the chance of an adverse effect on cell-mediated immunity is minimized.

The microcapsules which can be employed in the present invention comprise an oily liquid core material and a wall material and have been sensitized with antibody to antigen of lymphocyte, i.e., have become immunologically activated. The antibody is bound to microcapsules generally through a covalent bond between the wall material and antibody.

For binding antibody to the microcapsules, various conventional methods can be employed, e.g., an aldehyde cross linking method, an alkylation method, an isocyanate cross linking method, a maleimide cross linking method, a benzophenone cross linking method, a periodic cross linking method, etc., the details of which are described in Ichiro Chihata, *KOTEIKA KOSO* (Immobilized Enzyme), Kodansha Publishing Co., Ltd., (1975) and Eiji Ishikawa, *ENZYME IMMUNOASSAY*, pages 34 to 44. While the binding methods referred to are not limitative, it is important that antibodies are bound in such a way that they are not inactivated. The most typical method is to effect binding using aldehydes such as glutaraldehyde, formaldehyde, glyoxal, etc. According to this method, the microcapsules are mixed with 0.2 to 2% of, e.g., glutaraldehyde at temperatures of 15° to 40° C., preferably ambient temperature, for 1 to 2 hours, under normal pressure and the mixture is then washed with distilled water to remove the unreacted aldehyde. Next, the glutaraldehyde-treated microcapsules are mixed with 0.1 to 5% antibody, and reacted at room temperature for 1 to 2 hours. Specific examples of cross linking agents other than aldehydes include toluene-2,4-diisocyanate, N,N'-o-phenylenedimaleimide, m-maleimidobenzoyl, N-hydroxysuccinimide ester, etc.

In order to check if a bond is formed between the microcapsules and the antibody, a simple test can generally be performed by an immunofluorescene technique (*A Dictionary of Immunology*, page 128 (1979), published by Hirokawa Publishing Co., Ltd.) which comprises conjugating antibody to a fluorochrome and then allowing to react with the corresponding antigen in a tissue section or smear; the location of tissue antigens can thus be determined by observation of the pattern of fluorescence in the microscope.

Any material can be used as the wall of the microcapsules of the present invention, provided the material can bind to antibody without inactivating the antibody. Representative examples of wall materials are materials having an amino, imino, hydroxy or sulfhydryl group such as proteins (e.g., collagen, gelatin, casein, etc.); resins such as polyamino acid, polyacrylamide, polyamide, polyurethane, polyurea, polyurethane-urea, melamine resin, phenol resin, epoxy resin, silicone resin and derivatives thereof; cellulose and derivative thereof (e.g., methyl cellulose, ethyl cellulose, carboxymethyl cellulose, nitrocellulose, cellulose acetate, cellulose sulfate, etc.), gum arabic, starch, alginic acid and the like.

From a standpoint of easier discerniability and easier measurement, it is practically advantageous that the average size of the microcapsules is similar to that of lymphocyte; that is, it is preferred that the average size of the microcapsules be in a range of 1 μm to 10 μm. If the average size of the microcapsules is outside the range set forth above, it would be difficult to form rosettes and observe the rosettes.

Details of various wall materials and method for microencapsulation are described in, e.g., Asaji Kondo, *MICROCAPSULES*, Nikkan Kogyo Press, Tokyo (1970), Tamotsu Kondo and Masumi Koishi, *MICROCAPSULES*, Sankyo Publishing Co., Ltd., Tokyo (1972), etc.

Typical examples of oily liquid substances which can be core materials for the microcapsules are natural mineral oils, animal oils, vegetable oils and synthetic oils.

Specific examples of mineral oils are petroleum, kerosene, gasoline, naphtha, paraffin oil, etc. Animal oils typically include fish oil, lard, etc. Typical examples of vegetable oils include peanut oil, linseed oil, soybean oil, castor oil, corn oil, etc. Specific examples of synthetic oils are biphenyl compounds (e.g., isopropyl biphenyl, isoamyl biphenyl), terphenyl compounds (e.g., terphenyls of the type as described in German OLS No. 2,153,635), naphthalane compounds (e.g., diisopropylnaphthalene, compounds of the type as described in U.S. Pat. No. 4,003,589), alkylated diphenylalkanes (e.g., 2,4-dimethyldiphenylmethane, compounds of the type as described in U.S. Pat. No. 3,836,383), phthalic acid compounds (e.g., diethyl phthalate, dibutyl phthalte, dioctyl phthalate), etc. Using the thus prepared microcapsules, T cells and/or B cells can be determined independently or simultaneously, both in a very simple manner. When it is wished to identify or determine B cells alone, microcapsules are sensitized with an antibody having a receptor for B cells, E.g., anti-IgG antibody, and the microcapsules thus sensitized are applied to (e.g., mixed with) a testing sample containing lymphocytes. Then, rosettes formed by B cells and the microcapsules are determined by a microscopic observation. In the case of determining T cells, microcapsules are sensitized with an antibody having a receptor for T cells and the foregoing procedure is repeated.

Both T cells and B cells can be determined simultaneously in a single operation when microcapsules sensitized with an antibody having a receptor for B cells are used in combination with sheep red cells since sheep red cells selectively form rosettes with T cells. In this simultaneous measurement procedure, microcapsules having a receptor for T cells can also be used in place of sheep red cells. When two kinds of microcapsules, one being sensitized with an antibody having a receptor for B cells and another sensitized with an antibody having a receptor for T cells, are used for the simultaneous measurement procedure, the microcapsules form two kinds of rosettes with B cells and with T cells, respectively. These rosettes can be microscopically observed discriminatively.

The condition for the application of the microcapsules in accordance with the present invention to lymphocytes. i.e., the condition for forming rosettes, is not overly limited but generally at temperatures of from about 1° C. to about 40° C., preferably room temperature (about 18° C.) to 37° C., for about 10 minutes to about 24 hours, preferably 1 hour to 3 hours.

According to the present invention, (1) B cells and/or T cells can easily be determined using the microcapsules of the present invention with high detection sensitivity and high accuracy.

(2) In particular, B cells can easily be identified or determined in accordance with the method of the present invention, without requiring any complicated operation for the measurement and any expensive fluorescence microscope.

(3) B cells and T cells can easily be measured simultaneously in a single operation.

Hereafter the present invention will be described in more detail with reference to the examples below.

EXAMPLE 1

(1) Microcapsules (MC):

Microcapsules (average particle size: 5.0 μm) having urea resin at the surface thereof as the wall and having incorporated C.I. Solvent Blue 11 (C.I. #61525) in the core thereof (which were thus colored blue) were employed. The microcapsules had a specific gravity of 1.15 and an average diameter of about 5 μm and were negatively charged. The microcapsules were suspended in water in a proportion of 10 wt% solid content, which was used as a MC original suspension.

(2) Binding of Anti-Human IgG Antibody to MC:

The MC original suspension was washed twice with saline. The resulting residue was suspended in a 20-fold-diluted 0.1M tris-HCl buffer having pH of 8.6. To the suspension, 3.125% of glutaraldehyde was added in an equimolar amount. After allowing to react them at 37° C. for 30 minutes, the reaction mixture was washed twice with the same solvent (0.1M tris HCl-buffer) and the precipitate was suspended in 2-fold volume of the solvent. To the suspension, 5 mg of antibody (anti-human IgG rabbit IgG) was added and the reaction was performed at 37° C. for 1 hour. The reaction mixture was washed with the same solvent three times and suspended in a tris-HCl buffer containing 0.2% of glycine to obtain microcapsules sensitized with anti-human IgG antibody. The microcapsules thus prepared had an average diameter of about 5 μm.

EXAMPLE 2

(1) Microcapsules (MC):

Into 25 g of an oil mixture of 11.8 g of diisopropylnaphthalene and 13.2 g of chlorinated parrafin (chlorination degree 50%), 0.1 g of an ethylene diamine-propylene oxide addition product was dissolved. The solution was then ice-cooled. To this solution, 4 g of a 50% methyl ethyl ketone solution of Desmodur-L (tradename, manufactured by Bayer A.G., 1:4 addition product of tolylene diisocyanate and trimethylolpropane) was dissolved. The resulting oily solution was poured into 65 g of a 5% aqueous solution of polyvinyl alcohol (saponification degree, 88%; polymerization degree, 500) and the resulting mixture was emulsified with stirring. After the average droplet size reached about 7 μm, the emulsion was diluted with 100 g of water and the resulting mixture was reacted at 75° C. for 1 hour to microencapsulate the system. The thus obtained polyurethane-wall microcapsules were suspended in water in a proportion of 10 wt% solid content and used as a MC original suspension.

(2) Binding of Anti-Human IgG Antibody to MC:

In a manner similar to Example 1 (2), MC sensitized with anti-human IgG antibody was prepared except that anti-human IgG sheep IgG was employed in place of anti-human IgG rabbit IgG.

EXAMPLE 3

(1) Treatment with Poly-L-Lysine:

Each of cells of a microplate (#3034, manufactured by Farcon Co., Ltd.) was filled up with 40 μg/ml of poly-L-lysine (PLL, manufactured by Sigma Co., Ltd.) in an amount of 1 μl. After allowing the microplate to stand at room temperature for 60 minutes, the microplate was washed with distilled water and then dried to provide for use.

(2) Separation of Lymphocyte:

Lymphocytes were separated from heparin-added peripheral blood which was collected from the elbow vein of a volunteer, by means of the specific gravity centrifugation method using Ficoll-Isopaque in accordance with the Boyum's method. The thus separated lymphocytes were washed with distilled water three times. Thereafter, the concentration was adjusted to $1 \times 10^6$/ml.

(3) Measurement Using Microcapsules:

To the PLL-treated microplate described (1) above, 1.0 μl of the lymphocytes were adhered; the unreacted PLL was treated with fetal calf serum (FCS). To each of the cells of the microplate, 25 μl of the microcapsule suspension obtained in Example 1 (2) above was added to cause a reaction. Thereafter, the microplate was transposed and settled to eliminate unbound microcapsules with a flicking tube. The microcapsules bound to B cells of the lymphocytes to form a rosette. Subsequently, staining was performed with a fix-staining solution (a solution obtained by dissolving 0.25% of glutaraldehyde and 0.05% of Brilliant Cresyl Blue (C.I. #51010) in PBS was used as the staining solution). Lymphocytes were microscopically counted on the microplate and a rosette formation rate was determined per 200 lymphocytes in a conventional manner. The counting was all performed three times and the rosette formation rate was expressed by an average.

The B cell content in the lymphocytes separated from the blood of the volunteer's elbow vein was 19% in average.

EXAMPLE 4

Simultaneous Measurement of B Cells and T Cells:

The lymphocytes separated from the blood collected from the elbow vein of the volunteer described in Example 3 (2) were adhered to a PLL-treated microplate as described in Example 3 (1) in an amount of 1.0 μl. After the unreacted PLL was treated with FCS (fetal calf serum), 25 μl of the microcapsule suspension obtained in Example 1 (2) and 10 ml of a sheep red cell suspension (which was obtained by washing sheep red cells PBS three times and suspending them in FCS in a concentration of $2 \times 10^8$/ml) were added to each cell of the microplate to mix with the lymphocytes. After the mixture was reacted at room temperature for 90 minutes and further at 4° C. overnight, the microplate was transposed to remove excesses of or unbound microcapsules and sheep red cells. Thereafter, the fix-staining was performed using the fix-staining solution described in Example 3 (3). A microscopic observation indicated that two kinds of rosettes, i.e., rosettes formed by B cells and the microcapsules in such a shape that a B cell was surrounded by the microcapsules therearound, and rosettes formed by T cells and the sheep red cells in such a shape that a T cell was surrounded by the sheep red cells therearound, were present. Each of the rosette formation rates was determined as per 200 lymphocytes, in a conventional manner. The average of three runs showed that the B cell content was 19% and the T cell content was 81%.

COMPARISON EXAMPLE 1

Membrane Fluorescent Antibody Technique:

To 0.5 ml. of $2 \times 10^6$/ml of lymphocytes, 0.5 ml of FITC-labelled anti-human IgG rabbit serum (obtained by centrifuging antiserum manufactured by Boehring Co., Ltd. for 30 minutes at 10,000 r.p.m., filtering the centrifuged antisera using a microfilter having an average pore size of 0.22 μm and then diluting the filtrate with PBS by 10 times) was added. After reacting them at room temperature for 30 minutes, The reaction product was washed with PBS containing 5% of FCS three times. 200 lymphocytes were counted using a fluorescence microscope because it was impossible to count lymphocytes using an ordinary microscope. A percentage of lymphocytes emitting fluorescence (i.e., B cells) was thus determined by the membrane fluorescent antibody technique.

The B cell content was 19% in average but the results were widely distributed from 18 to 25%.

COMPARISON EXAMPLE 2

E Rosette Technique:

After the lymphocytes were adhered to a PLL-treated microplate in a manner as described in Example 3 (1), 10 ml of a sheep red cell suspension (obtained by washing sheep red cells with PBS three times and suspending them in fetal calf serum (FCS) in a concentration of $2 \times 10^8$/ml) was added and the reaction was allowed to cause at room temperature for 90 minutes and then at 4° C. overnight. The unbound sheep red cells were then removed. After rosettes formed by T cells and the sheep red cells in such a shape that a T cell was surrounded by the sheep red cells therearound were fix-stained, a rosette formation rate was determined. The T cell content was 81%.

According to the method of the present invention, the measurement of T cells and B cells could be simultaneously performed in a simple manner, and 81% of T cells and 19% of B cells were obtained stably with good reproducibility and accuracy (Example 4). In addition, macrophage was easily distinguishable and the judgment was not interefered at all.

The measurement of B cells alone could be effected by conventional microscopic observation (Example 3). As compared with the technique described in Comparison Example 1 which required a fluorescence microscopic observation, results were obtained in Example 3 with better reproducibility and higher accuracy in extremely simple operation.

While the invention has been described in detail and with reference to specific embodiments thereof, it will be apparent to one skilled in the art that various changes and modifications can be made therein without departing from the spirit and scope thereof.

What is claimed is:

1. A method for measuring cells based on cell-mediated immunity which comprises applying a microcapsule sensitized with antibody to antigen of lymphocyte and sheep red cells to lymphocyte at the same time and then independently measuring the distinguishable cells from each other.

2. The method as claimed in claim 1 wherein said antibody is selected from the group consisting of anti-IgG antibody, anti-IgM antibody and anti-IgA antibody.

3. The method as claimed in claim 1 wherein said cells are T cells and B cells.

4. The method as claimed in any of claims 1 to 3 wherein a rosette formation technique is utilized for the measurement of T cells and B cells.

5. A method for measuring cells based on cell-mediated immunity which comprises applying at least two kinds of microcapsules sensitized with at least two kinds of antibodies to antigens of lymphocytes that are optically distinguishable from each other to lymphocytes at the same time, and thereafter independently measuring cells that are optically distinguishable.

6. The method as claimed in claim 5 wherein one of said antibodies is selected from the group consisting of anti-IgG antibody, anti-IgM antibody and anti-IgA antibody and another is selected from the group consisting of anti-T antibody, antibody to brain common antigen and antibody to thymus common antigen.

7. The method as claimed in claim 6 wherein B cells are determined using the microcapsules sensitized with antibody selected from the group consisting of anti-IgG antibody, anti-IgM antibody and anti-IgA antibody and, T cells are determined using the microcapsules sensitized with antibody selected from the group consisting of anti-T antibody, antibody to brain common antigen and antibody to thymus common antigen.

8. The method as claimed in any of claims 5 to 7 wherein a rosette formation technique is utilized for the measurement of lymphocyte.

* * * * *